United States Patent [19]
Stahly

[11] Patent Number: 4,582,947
[45] Date of Patent: Apr. 15, 1986

[54] NUCLEOPHILIC DISPLACEMENT PROCESS FOR PREPARING 2,6-DIHYDROCARBONYL-4-(NITROARYL)-PHENOL

[75] Inventor: G. Patrick Stahly, Baton Rouge, La.

[73] Assignee: Ethyl Corporation, Richmond, Va.

[21] Appl. No.: 705,903

[22] Filed: Feb. 26, 1985

Related U.S. Application Data

[63] Continuation-in-part of Ser. No. 606,924, May 4, 1984, abandoned, Ser. No. 606,930, May 4, 1984, abandoned, Ser. No. 607,302, May 4, 1984, abandoned, and Ser. No. 607,305, May 4, 1984.

[51] Int. Cl.$^4$ .................... C07C 79/22; C07C 79/24
[52] U.S. Cl. .................... 568/707; 568/704
[58] Field of Search ............... 568/707, 704, 744, 708

[56] References Cited

U.S. PATENT DOCUMENTS 4,014,943  3/1977  Dounchis ..................... 568/707
4,172,151 10/1979  Moore ......................... 424/330

FOREIGN PATENT DOCUMENTS 2336551 12/1973  Fed. Rep. of Germany ...... 568/707

OTHER PUBLICATIONS

Korublum et al., "J. Organic Chem.", vol. 46(9), 1560–64 (1976).
Wright et al., "J. Organic Chem.", vol. 33(3), 1245–46 (1968).

Primary Examiner—Werren B. Lone
Attorney, Agent, or Firm—Donald L. Johnson; John F. Sieberth; Patricia J. Hogan

[57] ABSTRACT

2,6-Dihydrocarbyl-4-(nitroaryl)phenols are prepared by reacting (1) a nitroaromatic compound bearing a displaceable substituent selected from nitro and phenylsulfonyl on a ring carbon which is adjacent to, or separated by two ring atoms from, the ring carbon bearing the nitro substituent with (2) a 2,6-dihydrocarbylphenol selected from 2,6-di-t-butyl-, 2,6-di-t-amyl-, 2-t-butyl-6-isopropyl-, and 2,6-diphenylphenols having a replaceable hydrogen in the 4-position in an inert solvent and in the presence of a strong base. The preferred nitroaromatic compounds are 1,2- and 1,4-dinitrobenzenes, 1-nitro-2-phenylsulfonylbenzenes, and 1-nitro-4-phenylsulfonylbenzenes; and a preferred phenol is 2,6-di-t-butylphenol.

12 Claims, No Drawings

NUCLEOPHILIC DISPLACEMENT PROCESS FOR PREPARING 2,6-DIHYDROCARBONYL-4-(NITROARYL)-PHENOL

CROSS-REFERENCE TO RELATED APPLICATIONS

This application is a continuation-in-part of copending applications Ser. Nos. 606,924, now abandoned, 606,930, now abandoned, 607,302, now abandoned, and 607,305, all filed May 4, 1984.

FIELD OF INVENTION

This invention relates to 2,6-dihydrocarbyl-4-(nitroaryl)phenols and more particularly to a process for preparing them.

BACKGROUND

As indicated in Caronna et al., *Tetrahedron Letters*, No. 7, pp. 657–660 (1979), U.S. Pat. No. 4,172,151 (Moore), and German Offenlegungsscrift 2,336,551 (Sandoz), unsymmetrically substituted biphenyls are useful as pharmaceuticals, agricultural chemicals, antioxidants, specialty chemicals, and intermediates therefor; and they can be prepared by a variety of techniques.

Wright et al., *Journal of Organic Chemistry*, Vol. 33, No. 3, 1968, pp. 1245–1246, teach that one such unsymmetrically substituted biphenyl, i.e., 2,6-di-t-butyl-4-(p-nitrophenyl)phenol, can be prepared by reacting 2,6-di-t-butylphenol with p-chloronitrobenzene in an inert solvent and in the presence of a strong base. However, it has been found that no reaction occurs when m-chloronitrobenzene is substituted for p-chloronitrobenzene in such a reaction.

Kornblum et al., *Journal of Organic Chemistry*, Vol. 41, No. 9, 1976, pp. 1560–1564, teach that various nucleophiles are capable of displacing a nitro group of certain substituted nitrobenzenes in a dipolar aprotic solvent, such as hexamethylphosphoramide. 1,2-, 1,3-, and 1,4-Dinitrobenzenes and 4-nitrophenyl phenyl sulfone are exemplary of the substituted nitrobenzenes they employed; and their nucleophiles included, e.g., sodium benzenesulfinate, sodium thiophenoxide, sodium methoxide, sodium methyl mercaptide, etc.

SUMMARY OF INVENTION

An object of this invention is to provide a novel process for preparing 2,6-dihydrocarbyl-4-(nitroaryl)-phenols.

Another object is to provide such a process wherein the 2,6-dihydrocarbyl-4-(nitroaryl)phenols are prepared from 2,6-dihydrocarbylphenols and nitroaromatic compounds having a displaceable substituent on the aromatic ring.

These and other objects are attained by reacting (1) a nitroaromatic compound bearing a nitro substituent on a ring carbon which is adjacent to, or separated by two ring atoms from, a ring carbon which is a member of the same ring and which bears a displaceable substituent selected from nitro and phenylsulfonyl with (2) a 2,6-dihydrocarbylphenol selected from 2,6-di-t-butyl-, 2,6-di-t-amyl-, 2-t-butyl-6-isopropyl-, and 2,6-diphenylphenols having a replaceable hydrogen in the 4-position in an inert solvent and in the presence of a strong base so as to displace the displaceable substituent on the nitroaromatic compound with a 3,5-dihydrocarbyl-4-hydroxyphenyl group and form a 2,6-dihydrocarbyl-4-(nitroaryl)phenol.

DETAILED DESCRIPTION

Nitroaromatic compounds utilizable in the practice of the invention can be any of a variety of such compounds, the only requirement for their operability being that they be aromatic compounds bearing a nitro substituent on a ring carbon which is adjacent to, or separated by two ring atoms from, a ring carbon which is a member of the same ring and which bears a displaceable substituent selected from nitro and phenylsulfonyl. The portion of this requirement that the compounds be aromatic can be satisfied by the compounds' having a type of carbocyclic ring that is conventionally regarded as aromatic, e.g., a benzene ring, or by their having a 5- or 6-membered heterocyclic ring of aromatic character. Thus, the compounds may be characterized as compounds having one or more simple or fused, carbocyclic or heterocyclic aromatic rings, such as benzene, biphenyl, naphthalene, pyridine, quinoline, isoquinoline, thiophene, etc., rings, bearing the required substituents and optionally also bearing one or more inert substituents, i.e., substituents which will not prevent the displacement reaction from occurring. Inert substituents, when present, are usually selected from alkyl, alkenyl, alkynyl, cycloalkyl, aryl, alkaryl, or aralkyl groups, most commonly hydrocarbyl groups containing about 1–12 carbons.

Exemplary of the nitroaromatic compounds that may be employed are the 1,2- and 1,4-dinitrobenzenes, 1-nitro-2 or 4-phenylsulfonylbenzenes, 1-(2,3-dinitrophenyl)acetylene, 1-nitro-2-phenylsulfonyl-4-phenylbenzene, 1,4-dinitro-3-phenylbenzene, 1-nitro-2-(3-methylphenyl)-4-phenylsulfonylbenzene, 1,2- and 1,4-dinitronaphthalenes, 1-nitro-2 or 4-phenylsulfonylnaphthalenes, 2,3-, 3,4-, and 2,5-dinitropyridines, 2-nitro-3 or 5-phenylsulfonylpyridines, 2,3- and 3,4-dinitroquinolines, 4-nitro-3-phenylsulfonylquinoline, 1,4- and 3,4-dinitroisoquinolines, 3-nitro-4-phenylsulfonylisoquinoline, 2,3- and 3,4-dinitrothiophenes, 2-nitro-3-phenylsulfonylthiophene, etc.

The nitroaromatic compounds that are preferred vary with the products desired but are generally the 1,2- and 1,4-dinitrobenzenes and the 1-nitro-2 or 4-phenylsulfonylbenzenes.

When not commercially available, the nitroaromatic compounds may be prepared by conventional techniques, such as the techniques taught in March, *Advanced Organic Chemistry*, Second Edition, McGraw-Hill (New York), the teachings of which—especially the teachings on pages 475, 597, and 1110—are incorporated herein by reference. In general the dinitro compounds may be obtained by nitration of the appropriately substituted and protected aniline, followed by deprotection and oxidation of the desired isomer, and the phenylsulfonyl-substituted arenes may be prepared by displacement of chloride ion from the appropriately substituted nitrochloroarene by sodium benzenesulfinate.

2,6-Dihydrocarbylphenols that can be used in the invention, as indicated above, are the 2,6-di-t-butyl-, 2,6-di-t-amyl-, 2-t-butyl-6-isopropyl-, and 2,6-diphenylphenols that have a replaceable hydrogen in the 4-position, any other positions, when substituted, bearing inert substituents that will not interfere with the desired displacement reaction. The inert substituents, when present, are generally alkyl, alkenyl, alkynyl, cycloalkyl, aryl, aralkyl, or alkaryl groups, most commonly alkyl groups containing 1–6 carbons, such as methyl, ethyl, propyl, butyl, t-butyl, pentyl, hexyl, etc. A particularly preferred phenol is 2,6-di-t-butylphenol, and a few examples of other phenols that can be used are 2,6-di-t-butyl-3-methylphenol, 2,6-di-t-butyl-3-propylphenol, 2,3,6-tri-t-butylphenol, 1-(2,4-di-t-butyl-3-hydroxyphenyl)acetylene, 2,6-di-t-amylphenol, 2,6-di-t-amyl-3-ethylphenol, 2-t-butyl-6-isopropylphenol, 2-t-butyl-6-isopropyl-3-cyclohexylphenol, 2,6-diphenylphenol, 2,3,6-triphenylphenol, 2,6-diphenyl-3-benzylphenol, 2,6-diphenyl-3-(4-propylphenyl)phenol, and the like. Although the amount of this ingredient employed is not critical, it is generally desirable to use at least a stoichiometric amount of the phenol.

The solvent used in the reaction of the invention may be any solvent that is inert under the conditions of the reaction, i.e., any solvent that will not prevent the reaction from occurring. Exemplary of the solvents that can be used are inert liquid hydrocarbons, such as benzene, toluene, xylene, hexane, heptane, isooctane, etc.; ethers, such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines, such as pyridine, N-ethylpiperidine, triethylamine, tributylamine, N,N-diphenyl-N-methylamine, N,N-dimethylaniline, etc.; alcohols, such as methanol, ethanol, propanol, etc.; nitriles, such as acetonitrile, etc. However, the preferred solvents are dipolar aprotic solvents, such as dimethylsulfoxide, dimethylsulfone, tetramethylene sulfone, N,N-dimethylformamide, N,N-dimethylacetamide, N-methylpyrrolidone, etc.

Bases useful in the practice of the invention include all bases strong enough to activate the reactants but are generally alkali or alkaline earth metal hydrides, hydroxides, or alkoxides, such as sodium, potassium, calcium, barium, or magnesium hydride or hydroxide, sodium methoxide, potassium t-butoxide, etc. The preferred bases are the alkali metal hydrides, hydroxides, and alkoxides. If desired, the base can be used in conjunction with a phase transfer catalyst, such as a quaternary ammonium salt, a polyethylene glycol, or a suitable crown ether, as in similar processes known in the art. It is preferable to employ at least one molar proportion of base per molar proportion of the nitroaromatic compound, generally a molar excess of the base.

The reaction of the invention results in the formation of a 2,6-dihydrocarbyl-4-(nitroaryl)phenol by a mechanism whereby the phenol displaces the displaceable substituent of the nitroaromatic compound. It may be conducted at any suitable temperature, the most appropriate temperature varying with the strength of the base and reactivities of the reactants employed, to prepare the product in a matter of minutes or a few hours. Ambient temperatures are satisfactory when the strongest bases and/or more reactive reactants are used, but higher temperatures, e.g., temperatures up to about 200° C., are more appropriate when somewhat weaker bases and/or less reactive reactants are utilized.

The following examples are given to illustrate the invention and are not intended as a limitation thereof.

EXAMPLE I

A mixture of 30 mg (0.75 mmol) of powdered sodium hydroxide, 100 mg (0.59 mmol) of 1,2-dinitrobenzene, 155 mg (0.75 mmol) of 2,6-di-t-butylphenol, and 1.0 mL of dimethylsulfoxide was heated at 60° C. for 17 hours and poured into 10 mL of 1N HCl, and the resulting aqueous mixture was extracted with three 10 mL portions of diethyl ether. The ether layers were combined, dried over magnesium sulfate, and concentrated. Purification of the residue by preparative thin layer chromatography (tlc) afforded 206 mg of crude 2,6-di-t-butyl-4-(2-nitrophenyl)phenol.

EXAMPLE II

Example I was repeated except that the 1,2-dinitrobenzene was replaced with 1,4-dinitrobenzene, and the reaction was conducted at 80° C. for three hours. Purification of the residue by preparative tlc and crystallization afforded 125 mg (64% yield) of 2,6-di-t-butyl-4-(4-nitrophenyl)phenol.

EXAMPLE III

Example I was repeated except that the 1,2-dinitrobenzene was replaced with 1-nitro-2-phenylsulfonylbenzene, and the reaction was conducted at 80° C. for 20 hours. Purification of the residue by preparative tlc afforded 131 mg of crude 2,6-di-t-butyl-4-(2-nitrophenyl)phenol.

EXAMPLE IV

Example I was repeated except that the 1,2-dinitrobenzene was replaced with 1-nitro-4-phenylsulfonylbenzene, and the reaction was conducted at 80° C. for 30 hours. Purification of the residue by preparative tlc afforded 133 mg of crude 2,6-di-t-butyl-4-(4-nitrophenyl)phenol.

It is obvious that many variations can be made in the products and processes set forth above without departing from the spirit and scope of this invention.

I claim:

1. A process which comprises reacting (1) a nitroaromatic compound bearing a nitro substituent on a ring carbon which is adjacent to, or separated by two ring atoms from, a ring carbon which is a member of the same ring and which bears a displaceable substituent selected from nitro and phenylsulfonyl with (2) a 2,6-dihydrocarbylphenol selected from 2,6-di-t-butyl-2,6-di-t-amyl-, 2-t-butyl-6-isopropyl-, and 2,6-diphenyl-phenols having a replaceable hydrogen in the 4-position at a temperature in the range of ambient temperature up to about 200° C. in an inert solvent and in the presence of a strong base selected from alkali and alkaline earth metal hydrides, hydroxides, and alkoxides so as to displace the displaceable substituent on the nitroaromatic compound with a 3,5-dihydrocarbyl-4-hydroxyphenyl group and form a 2,6-dihydrocarbyl-4-(nitroaryl)-phenol; the amount of base employed being at least one molar proportion per molar proportion of the nitroaromatic compound.

2. The process of claim 1 wherein the aromatic ring bearing the nitro and displaceable substituents is a heterocyclic ring having five or six members.

3. The process of claim 1 wherein the aromatic ring bearing the nitro and displaceable substituents is a carbocyclic ring.

4. The process of claim 3 wherein the nitroaromatic compound is a nitrobenzene.

5. The process of claim 4 wherein the nitrobenzene is 1,2-dinitrobenzene.

6. The process of claim 4 wherein the nitrobenzene is 1,4-dinitrobenzene.

7. The process of claim 4 wherein the nitrobenzene is 1-nitro-2-phenylsulfonylbenzene.

8. The process of claim 4 wherein the nitrobenzene is 1-nitro-4-phenylsulfonylbenzene.

9. The process of claim 1 wherein the 2,6-dihydrocarbylphenol is a phenol having substituents only on the 2- and 6-positions.

10. The process of claim 9 wherein the 2,6-dihydrocarbylphenol is 2,6-di-t-butylphenol.

11. The process of claim 9 wherein the 2,6-dihydrocarbylphenol is 2,6-diphenylphenol.

12. The process of claim 1 wherein the strong base is an alkali metal hydride, hydroxide, or alkoxide.

* * * * *

UNITED STATES PATENT AND TRADEMARK OFFICE
CERTIFICATE OF CORRECTION

PATENT NO. : 4,582,947
DATED : APRIL 15, 1986
INVENTOR(S) : G. PATRICK STAHLY

It is certified that error appears in the above-identified patent and that said Letters Patent is hereby corrected as shown below:

Title, line 3, " 2,6-DIHYDROCARBONYL-4-(NITROARYL)- "
  should read -- 2,6-DIHYDROCARBYL-4-(NITROARYL)- --.

Signed and Sealed this

Nineteenth Day of August 1986

[SEAL]

Attest:

DONALD J. QUIGG

Attesting Officer

Commissioner of Patents and Trademarks